(12) United States Patent
Chandrasekaran et al.

(10) Patent No.: US 8,229,537 B2
(45) Date of Patent: Jul. 24, 2012

(54) MOTION ARTIFACT REJECTION MICROELECTRODE

(75) Inventors: Shankar Chandrasekaran, Chennai (IN); Juha Virtanen, Helsinki (FI); Shivappa Goravar, Bangalore (IN)

(73) Assignee: General Electric Company, Schenectady, NY (US)

( * ) Notice: Subject to any disclaimer, the term of this patent is extended or adjusted under 35 U.S.C. 154(b) by 90 days.

(21) Appl. No.: 12/725,865

(22) Filed: Mar. 17, 2010

(65) Prior Publication Data

US 2011/0230745 A1 Sep. 22, 2011

(51) Int. Cl.
*A61B 5/04* (2006.01)
*A61B 5/0478* (2006.01)
*A61B 5/11* (2006.01)

(52) U.S. Cl. ........ 600/372; 600/383; 600/396; 600/544; 600/595

(58) Field of Classification Search .......... 600/372, 600/373, 383, 396, 544, 595
See application file for complete search history.

(56) References Cited

U.S. PATENT DOCUMENTS

| | | | | |
|---|---|---|---|---|
| 4,969,468 | A * | 11/1990 | Byers et al. | 600/373 |
| 5,513,649 | A | 5/1996 | Gevins et al. | |
| 5,978,693 | A * | 11/1999 | Hamilton et al. | 600/391 |
| 6,622,035 | B1 | 9/2003 | Merilainen et al. | |
| 6,881,191 | B2 * | 4/2005 | Oakley et al. | 600/483 |
| 6,912,414 | B2 * | 6/2005 | Tong | 600/372 |
| 6,961,603 | B2 * | 11/2005 | Merilainen | 600/383 |
| 7,395,105 | B2 * | 7/2008 | Schmidt et al. | 600/372 |
| 2008/0139911 | A1 | 6/2008 | Chandrasekaren et al. | |

FOREIGN PATENT DOCUMENTS

EP  1164928  6/2005

* cited by examiner

*Primary Examiner* — Lee S Cohen
(74) *Attorney, Agent, or Firm* — Andrus, Sceales, Starke & Sawall, LLP

(57) ABSTRACT

An electrode system for the measurement of biopotential signals includes a substrate. A microelectrode is coupled to the substrate. An accelerometer is coupled to the substrate. A biopotential amplifier is electrically coupled to the microelectrode and acceleration measurement circuit is electrically coupled to the accelerometer. A method of measuring a biopotential from a patient includes sensing a biopotential with a microelectrode. The biopotential is amplified with an amplifier in electrical communication with the microelectrode. A movement of the electrode is sensed with an accelerometer integrated with the electrode substrate. The sensed biopotential and the sensed movement are provided to an electronic controller. Portions of the sensed biopotential that correspond to sensed movement are identified as artifact contaminated portions.

13 Claims, 9 Drawing Sheets

MOTION ARTIFACT REJECTION MICROELECTRODE

BACKGROUND

The present disclosure is related to the field of biopotential transduction. More specifically, the present disclosure is related to a biopotential microelectrode with motion artifact rejection.

Electrodes applied to the skin of a patient are commonly employed to non-invasively obtain biopotential signals that are useful in determining a physiological condition or functioning of a patient. The anatomy of mammalian skin presents a high electrical impendence. This electrical impedance decreases the magnitude and the signal to noise ratio of the biopotential signal obtained by the electrode. It is common to abrade the skin and/or apply electrolytic gel to skin before using the electrode to improve the electrical characteristics of the signal.

An alternative to applying an electrolytic gel is to form spikes on the electrode that penetrate the outer layer of the skin which reduce the impedance of the electrode-skin interface. However, even after improving the electrical characteristics of the electrode-skin interface, motion artifacts are a significant source of error in an acquired biopotential signal. Motion artifacts are caused by motion of the patient, the electrode, or the wire that transmits the acquired biopotential signal back to a signal processor.

BRIEF DISCLOSURE

The present disclosure is related to a microelectrode system for the measurement of biopotential signals. The microelectrode system includes a substrate with a microelectrode extending from the substrate. An accelerometer is integrated with the substrate. The accelerometer produces an acceleration signal indicative of an acceleration of the substrate. Accelerometer measurement circuitry is electrically coupled to the accelerometer.

A method of measuring a biopotential from a patient includes sensing a biopotential with a microelectrode. The biopotential is amplified with an amplifier in electrical communication with the microelectrode. A movement of the electrode is sensed with an accelerometer that is integrated with an electrode substrate. The sensed biopotential and the sensed movement are provided to an electronic controller.

A biopotential electrode disclosed herein includes a silicon substrate. A microelectrode is deposed on the silicon substrate. An accelerometer is integrated with the silicon substrate. The accelerometer includes a proof mass etched from the silicon substrate. The proof mass is suspended from the substrate by at least one support.

BRIEF DESCRIPTION OF THE DRAWINGS

The drawings illustrate the best mode presently contemplated of carrying out the disclosure. In the drawings.

DETAILED DISCLOSURE

Skin mounted monitoring electrodes are typically used to obtain biopotentials. The human skin is made of three distinct layers: stratum corneum, viable epidermis, and dermis. The outer 10-15 micrometers of skin, called the stratum corneum, is dead tissue that forms the primary barrier for the body. The statum corneum is the major contributor to skin impedance and is a major factor in the signal to noise ratio characteristic of skin-mounted electrodes. Below the stratum corneum lies the viable epidermis (50-100 micrometers). The viable epidermis comprises living cells, but contains few nerves and is devoid of blood vessels. Penetration of the skin to the viable epidermis is painless since the nerves are found in deeper tissues. Below the viable epidermis is the dermis. The dermis forms the bulk of skin volume and contains living cells, nerves, and blood vessels.

Microelectrodes reduce skin impedance using a plurality of electrically conductive spikes that are capable of penetrating through the stratum corneum and into the viable epidermis. The electrode spikes typically range from 50-250 micrometers in length, and are arranged in arrays between 100-10,000 spikes. The spikes are of a necessary degree of sharpness such as to penetrate the statum corneum and the viable epidermis.

Figure 1:
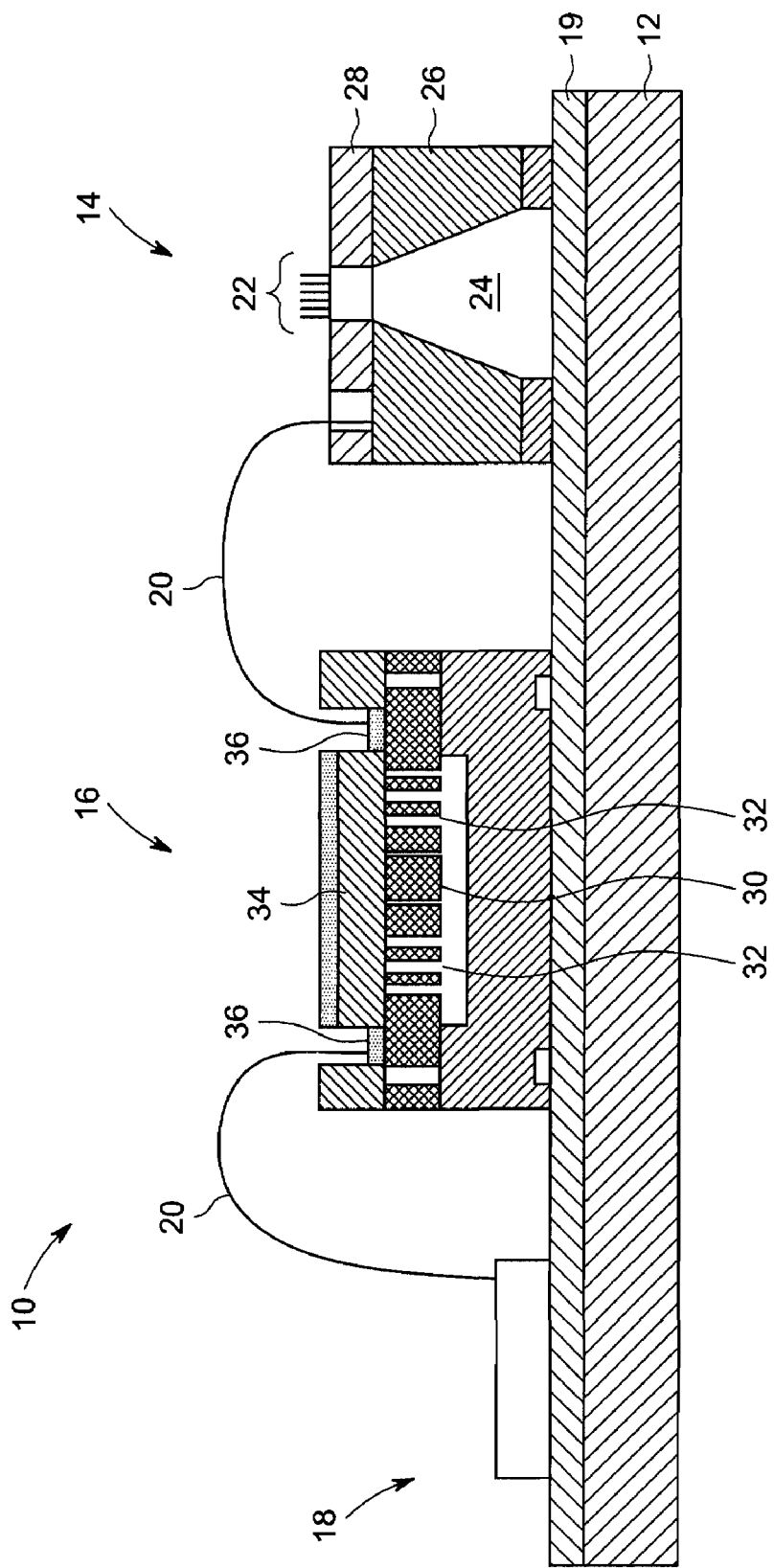
FIG. 1 depicts a horizontally aligned microelectrode embodiment.

FIG. 1 depicts an embodiment of an electrode 10. The electrode 10 embodies a horizontally stacked arrangement whereby each of the components are aligned horizontally on a base substrate 12. The base substrate 12 may be constructed of silicon material.

The electrode 10 further includes three components that are coupled the base substrate 12. These three components include a microelectrode 14, an accelerometer 16, and electronics 18.

In the present application, the interactions of some components are described as being coupled. The term coupled is used in this application to include mechanical or electrical connections and direct or indirect connections.

The electrode 10 of FIG. 1 arranges the microelectrode 14, accelerometer 16, and electronics 18 as separate components that are horizontally aligned on the base substrate 12. Some embodiments may include an insulative layer 19 between the components (14, 16, 18) and the base substrate 12. The microelectrode 14, the accelerometer 16, and the electronics 18 are electrically connected using wires 20 connecting the components. It is alternatively understood that another form of electrical connection between the microelectrode 14, accelerometer 16, and electronics 18 may alternatively be used. Such alternative forms of electrical connection may include, but are not limited to, printed connections on the base substrate 12.

The microelectrode 14 includes a plurality of spikes 22 that are electroplated with silver (Ag) or silver/silver chloride (Ag/AgCl). In case of pure silver coating, the surface is passively covered over time with a layer of silver chloride. The Ag/AgCl coating improves the electrical conductance of the spikes 22 by converting the ionic currents in tissue into movement of electronics in metallic conductors. The spikes 22 range in length between 50-250 micrometers. This range of lengths is suited to both penetrate the stratum corneum and into the viable epidermis, yet offer enough range in spike length such that a sufficient number of spikes penetrate the viable epidermis despite imperfections in the skin of the patient.

The microelectrode 14 is created by etching an electrode cavity 24 out of a silicon substrate 26, and depositing the spikes 22 on a layer of doped boron 28. This process will be described in greater detail herein.

As recognized above, the penetration of the stratum corneum by the spikes 22 provides improved signal to noise ratio of the biopotential acquired by the electrode 10. Another significant source of error in acquired biopotentials are motion artifacts. As noted above, motion artifacts can arise from movement of the patient, movement of the electrode, or movement of the lead wires (not depicted) extending from the electrode to a monitoring device (not depicted). Motion artifact detection can be used to flag likely contaminated biopotential data, incorporated into an index of biopotential signal quality, or signal processing may be employed to remove the estimated motion artifact from the acquired biopotential. The electrode 10 is able to achieve improved biopotential acquisition with the integration of an accelerometer 16 in the electrode 10. By locating the accelerometer 16 on the electrode 10, the accelerometer can measure motion experienced by the electrode 10, resulting in improved estimation of the motion artifacts present in the acquired biopotential.

The accelerometer includes a proof mass (not depicted) that is suspended from the accelerometer 16 by a plurality of springs 30. A plurality of electrodes 32 are strategically arranged such that acceleration of the proof mass may be measured. Specific embodiments and configurations of the accelerometer will be disclosed in further detail herein.

The accelerometer 16 is covered by a shadow mask 34 that protects the accelerometer components and provides electrical and deposition isolation. Contact pads 36 on the accelerometer 16 enable electrical connections between the components, such as by wires 20. A wire 20 connects from a contact pad 36 on the accelerometer 16 to the electronics 18. The Embodiments of the electronics 18 will be described in greater detail herein, particularly with respect to FIG. 4.

Figure 2:
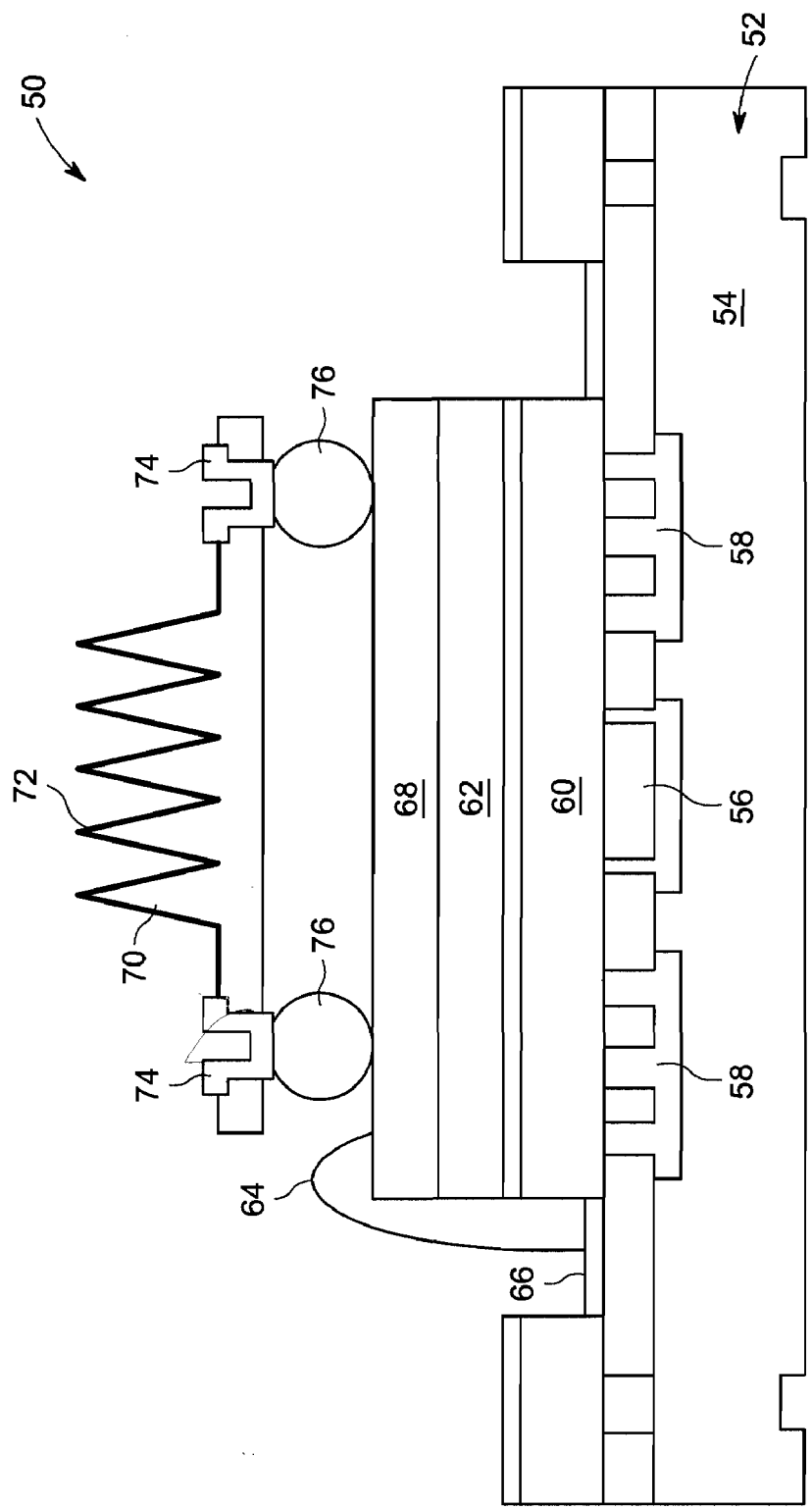
FIG. 2 depicts a vertically aligned microelectrode embodiment.

FIG. 2 depicts an alternative embodiment of an electrode 50. The electrode 50 is arranged in a vertical stacked arrangement which is an alternative orientation to the horizontal arrangement of the electrode 10 depicted in FIG. 1. In the vertical stacked arrangement of electrode 50, an accelerometer 52 is constructed from a silicon substrate 54. As described above with respect to FIG. 1, the accelerometer includes a proof mass (not depicted) suspended from the substrate 54 by a spring 56 and strategically located electrodes 58 for sensing the acceleration or displacement of the proof mass.

A shadow mask 60 is deposited on top of the accelerometer 52 to protect the accelerometer. A further insulating layer 62 is located on top of the shadow mask 60 to provide additional electrical isolation between the accelerometer 52 and the components stacked above it. A wire 64 extends from a contact pad 66 on the accelerometer 52 up to electronics 68 that are located above the insulating layer 62. The wire 64 provides an electrical connection between the accelerometer 52 and the electronics 68. A spiked electrode 70 is further stacked on top of the electronics 68. The spiked electrode 70 is covered by silver or silver/silver chloride electroplating 72 in order to improve the conductance of the spiked electrode 70. The spiked electrode 70 is electrically connected to the electronics 68 by through hole 74 and solder bump 76.

FIGS. 1 and 2 present alternative embodiments for the integrated electrodes disclosed herein and both the embodiments, as well as alternatives to these specifically disclosed configurations, are considered within the scope of the disclosure.

Figure 3A:
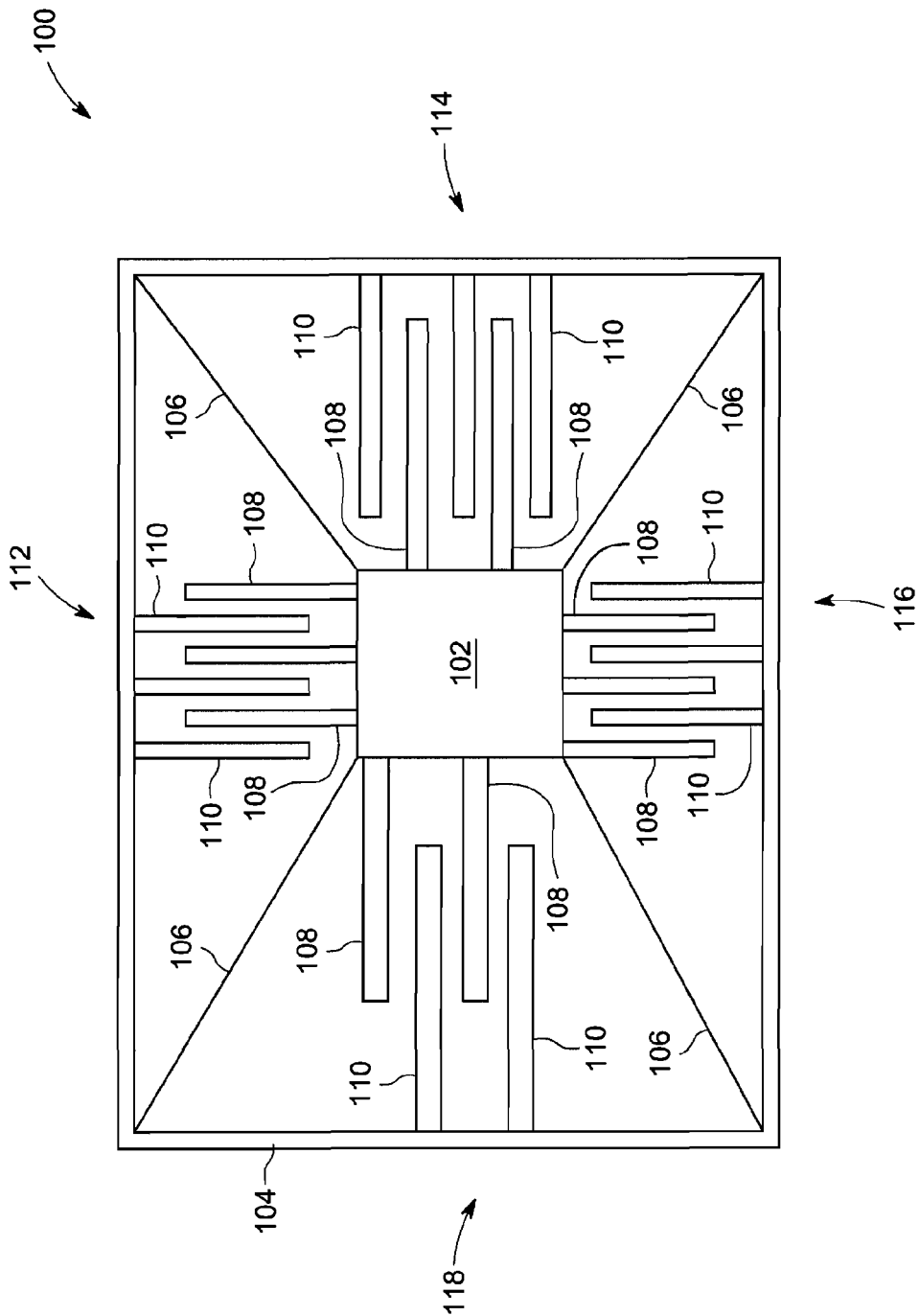
FIGS. 3A and 3B depict alternative accelerometer embodiments.
Figure 3B:
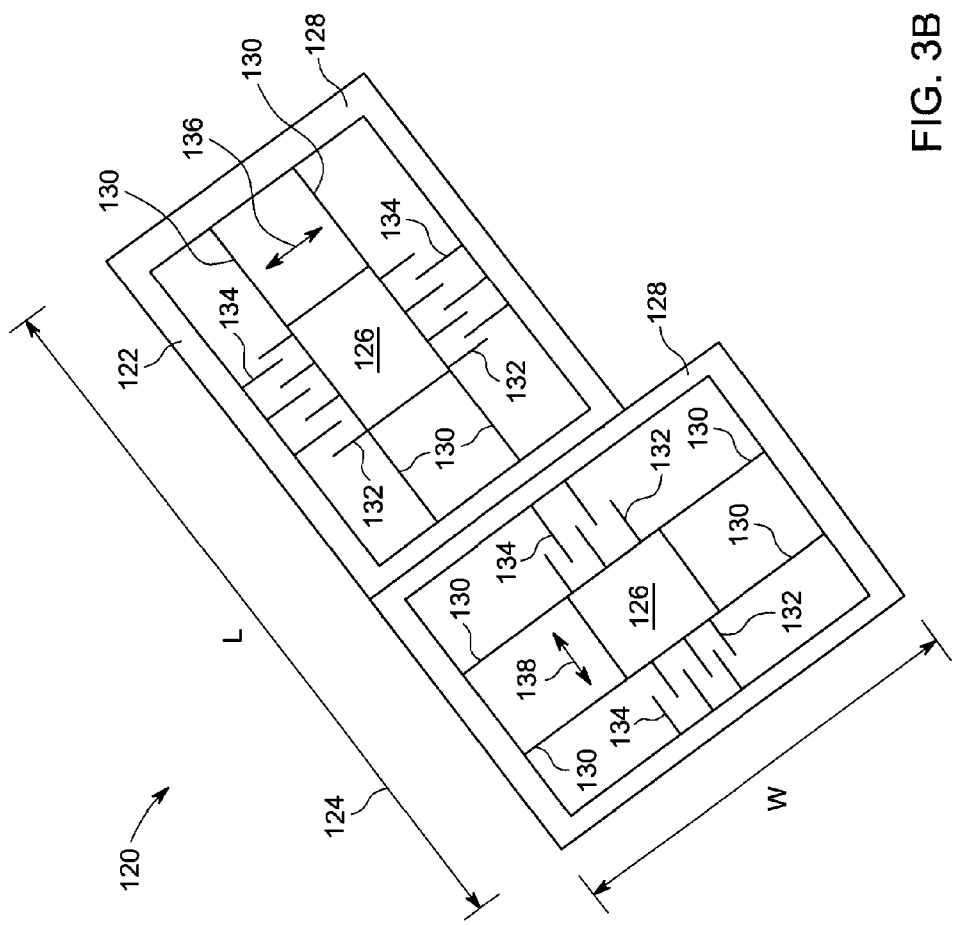

FIGS. 3A and 3B depict alternative embodiments of the presently disclosed accelerometer, incorporated into the presently disclosed electrode embodiments.

FIG. 3A depicts an accelerometer 100 assigned to detect acceleration in two perpendicular directions. While an accelerometer that measures acceleration in all three perpendicular directions may be desirable in some embodiments, through the use of signal processing and strategic accelerometer design, accelerometers measuring acceleration in two or even one direction may be effectively used in electrode embodiments is disclosed herein. Therefore, while the accelerometers of FIGS. 3A and 3B are designed for measuring acceleration in two perpendicular directions, it is understood that these designs may be modified to measure acceleration in one or three perpendicular directions and fall within the scope of the present disclosure.

The accelerometer 100 of FIG. 3A includes a proof mass 102 that is constructed of silicon as will be disclosed in further detail herein, particularly with respect to FIG. 5. The proof mass is suspended from a support frame 104 by a plurality of spring supports 106.

A plurality of capacitive or resistive sensors or electrodes extend from both the proof mass 102 and the frame 104 in orthogonal directions. The displacement of the proof mass 102 due to the acceleration of the accelerometer 100 is measured by the changes in capacitance (or impedance) between the electrode 108 extending from the proof mass and the electrode 110 extending from the frame 104.

While the accelerometer 100 of FIG. 3A is depicted with four sets (112, 114, 116, 118) of electrodes (108, 110) with two sets (112, 116) (114, 118) aligned in either direction, it is understood that alternative embodiments may only use a single set of aligned electrodes 108, 110, in each direction. For example, the accelerometer 100 may alternatively be implemented with electrode sets 112 and 114, or another similar variant.

FIG. 3B depicts an alternative embodiment of an accelerometer 120. The accelerometer 120, rather than configuring a single proof mass to detect acceleration in multiple directions as in accelerometer 100, accelerometer 120 is constructed of two perpendicularly aligned accelerometers such as a length-aligned accelerometer 122 and a width-aligned accelerometer 124. Each of the accelerometers 122, 124 includes a proof mass 126 that is suspended from a frame 128 by a plurality of springs 130. Elongate electrodes 132 or sensors extend from the proof mass 126. Additionally, electrodes 134 or sensors extend from the frame 128 in parallel to the electrodes 132 extending from the proof mass 126. The electronics (FIG. 1), connected to the accelerometer 120, sense the change in capacitance between the elongated electrodes 132 and 134. This is indicative of the displacement and acceleration of the proof mass 126.

The proof mass 126 of the length-aligned accelerometer 122 is displaced due to acceleration in the direction of arrow 136. The proof mass 126 of the width-aligned accelerometer 124 is displaced due to acceleration in the direction of arrow 138.

As an exemplary embodiment, the accelerometer 120 may have the overall dimension of 2.25 millimeter in the length direction (L) and 1.5 millimeters in the width direction (W). Exemplary dimensions of one of the accelerometers 122, 124 may be 1.5 millimeters length, 0.5 millimeters width and 0.3 millimeters height. However, these dimensions are intended to be limiting on the scope of the size and/or construction of the accelerometers used in the presently disclosed electrode.

Figure 4A:
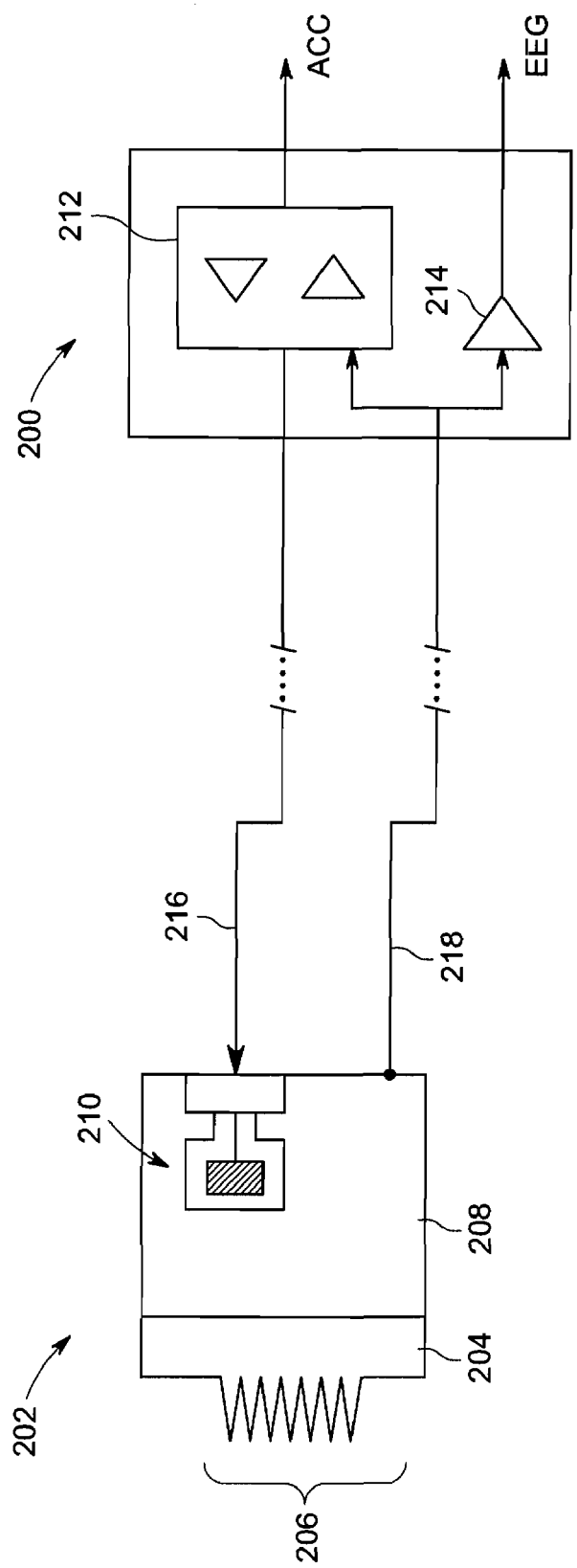
FIGS. 4A-C depict alternative accelerometer circuits.
Figure 4B:
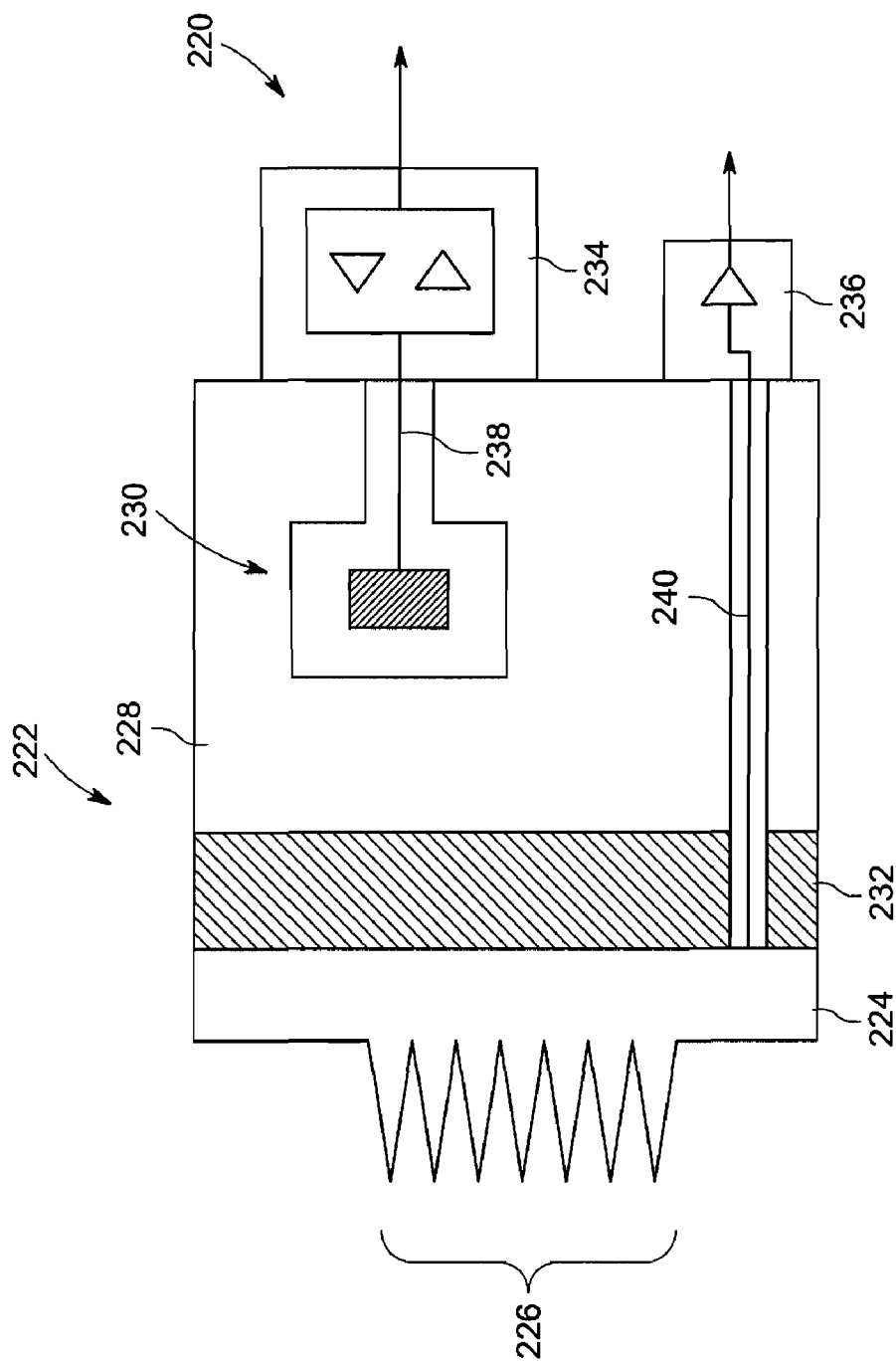

FIGS. 4A and 4B generally depict alternative embodiments of the electronics used in conjunction with the electrode disclosed herein.

In FIG. 4A, the electronics 200 are separate from the electrode 202. As described above, the electrode 202 includes a microelectrode 204 with a plurality of spikes 206. The microelectrode 204 is connected to a substrate 208 with an accelerometer 210.

The electronics 200 include an acceleration measurement circuit 202 and a biopotential amplifier 214. In an exemplary embodiment, the biopotential is an electroencephalogram (EEG); however, it is understood that alternative embodiments may be used to acquire electrocardiograph (ECG), electromyograph (EMG), or any other biopotentials.

The acceleration measurement circuit 212 provides a supply voltage which is provided through a first electrical lead 216 to the accelerometer 210. The supply voltage is, for example, a sine wave at a frequency of 100 KHz. Such a high frequency power supply is suitable for the size and construction of the accelerometer 210 as disclosed herein. The supply voltage is supplied to the accelerometer 210 and a return signal is provided back to the electronics 200 on a second electrical lead 218. The return signal may be a combined signal that includes both the biopotential signal acquired by the microelectrode 204 and the acceleration signal from the accelerometer 210. The combined signal is provided to both the acceleration measurement circuit 212 and the biopotential amplifier 214. In this embodiment, the high frequency supply voltage provided to the accelerometer 210 results in the acceleration portion of the combined signal to also be of a high frequency. The biopotential signal on the other hand has a frequency content in a low frequency range, for example, between 0.5 and 150 Hz. Therefore, the acceleration measurement circuit 212 is designed to appear as a high impedance to low frequency signals, such as the biopotential signal and the biopotential amplifier 214 is designed to appear as a high impedance to high frequency signals, such as the acceleration signal. This effective splits the combined signal into the acceleration and biopotential portions within the electronics 200 for the processing of each of these signals.

The acceleration measurement circuit 212 may measure the displacement of the accelerometer 210 in a variety of ways. The acceleration measurement circuit 212 may measure the changes in capacitance as the electrodes of the accelerometer 210 change in orientation to one another. Alternatively, the acceleration measurement circuit 212 may measure capacitance imbalance generated on opposite sides of the accelerometer 210 as the proof mass is displaced. In a still further embodiment, the acceleration measurement circuit 212 is used to detect the relatively low frequency signal of the proof mass motion as an envelope on the high frequency (100 KHz) portion of the combined signal.

As depicted in FIG. 4A, the first electrical lead 216 and second electrical lead 218 connect the electronics 200 to the electrode 202. The length of first electrical lead 216 and second electrical lead 218 may therefore be anywhere from a few centimeters in length to one meter or more in length. The first electrical lead 216 and second electrical lead 218 can be implemented as a wire in a cable form, or alternative embodiments may use wireless connections.

FIG. 4B depicts an alternative embodiment of the electronic 220 and the electrode 222 as disclosed herein.

The electrode 222 includes a microelectrode 224 which comprises a plurality of electrically conductive spikes 226.

The electrode 222 further includes a substrate 228 in which an accelerometer 230 is formed. An insulative layer 232 is connected between the microelectrode 224 and the substrate 228 in order to provide electrical isolation between the microelectrode 224 and the substrate 228.

The electronics 220 comprise an acceleration measurement circuit 234 and a biopotential amplifier 236. The electronics 220 are mechanically and electronically connected to the electrode 222. In the embodiment depicted, the electronics 220 are mechanically connected to the substrate 228 and the accelerometer 230 is electrically connected to the acceleration measurement circuit 234 by an electrical connection 238. Similarly, the microelectrode 224 is electrically connected to the biopotential amplifier 236 by an electrical connection 240.

Figure 4C:
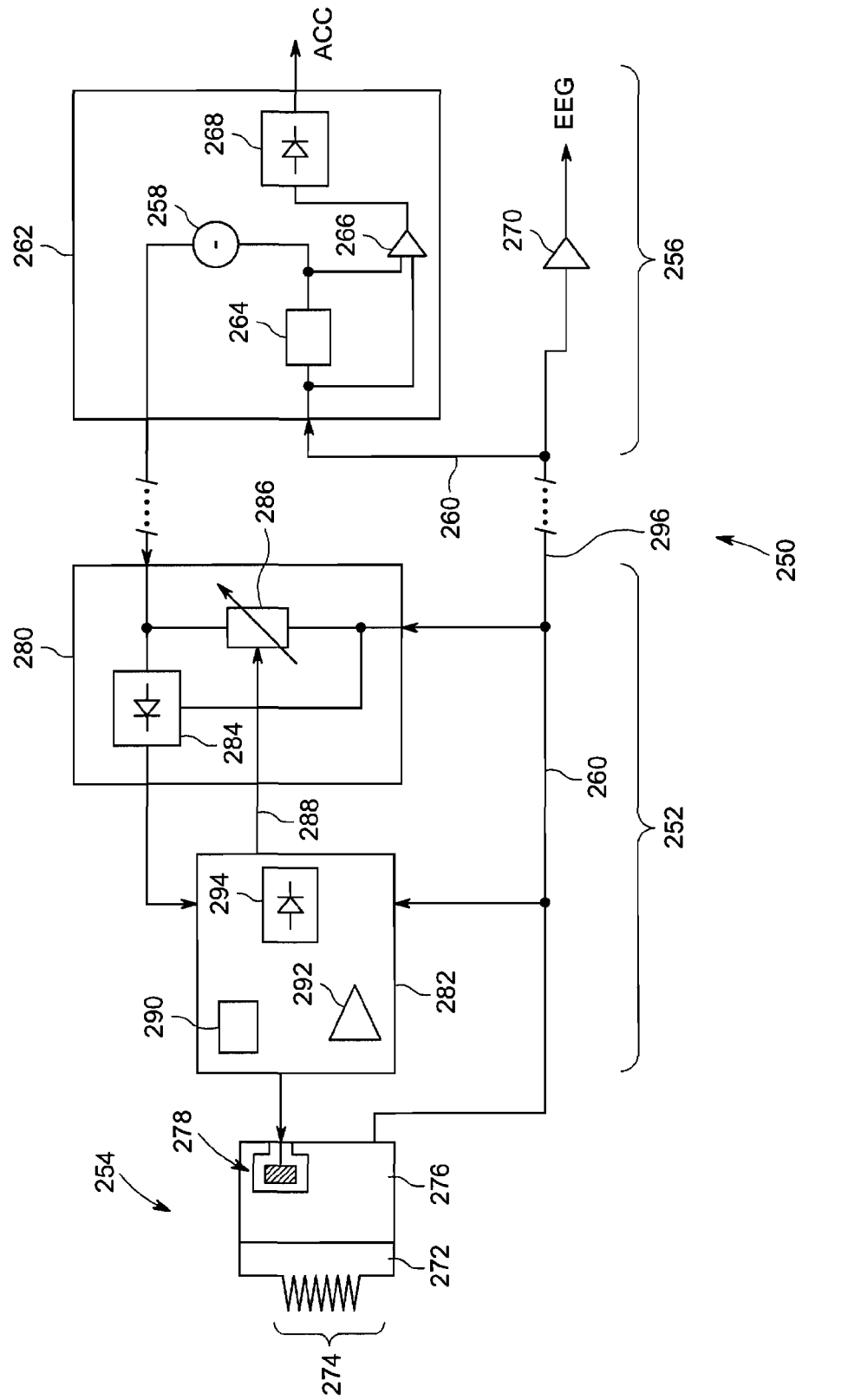

FIG. 4C depicts a further embodiment of the electrode and electronics as disclosed herein. In comparison to the systems previously disclosed with respect to FIGS. 4A and 4B with system of 4C depicts a hybrid implementation that splits the electronics 250 into a front end 252 that is mechanically connected to the electrode 254 and a back end 256 that is a distance from the front end 252, but still electrically connected to the front end 252 and the electrode 254.

The back end 256 includes an AC voltage source 258. The AC voltage source 258 supplies AC voltage at an exemplary frequency of about 100 KHz or more to the front end electronics 252 and the electrode 254. The back end electronics 256 receive an electrode signal 260 that, in an embodiment, includes both acceleration signal data and biopotential signal data. The acceleration signal data may be in the form of an amplitude modulated current signal.

The acceleration measurement electronics 226 of the back end 256 may therefore be designed to appear as a high impedance to low frequency signals, for example, a biopotential. By an exemplary embodiment, the biopotential may have a frequency content between 0.5 Hz and 150 Hz. The design of the acceleration measurement electronics 226 therefore effectively filters the biopotential signal out of the electrode signal 260 as it enters the acceleration measurement electronics 262. Inside the acceleration measurement electronics 262, a shunt resistor 264 and an amplifier 266 process the current of the electrode signal 260. This is provided to an acceleration detector 268 that determines the sensed acceleration by evaluating, in an embodiment, an envelope of the amplitude modulated current signal.

A biopotential amplifier 270 is further connected to the electrode signal 260. Opposite to the acceleration measurement electronics 262, the biopotential amplifier 270 may be designed to appear as a high impedance to high frequency signals, and therefore the biopotential amplifier 270 only amplifies the biopotential signal portion of the electrode signal 260. Alternatively, separate acceleration and biopotential signals (not depicted) may be acquired off of the electrode 254.

The electrode 254 includes a microelectrode 272 with a plurality of electrically conductive spikes 274. The microelectrode 272 is connected to a substrate 276 within which an accelerometer 278 is formed. The electrode 254 is connected to the front end electronics 252 which includes a voltage supply 280 and a acceleration circuit 282. The voltage supply 280 includes a rectifier 284 and a variable power source 284. The variable power source 284 may be implemented as a voltage controlled circuit source or a voltage controlled load. The variable power source 286 receives the electrode signal 260 and an acceleration signal 288 from the acceleration circuit 282 in a feedback loop. The variable power source 286 and the rectifier 284 process the AC supply voltage provided by the AC power supply 258. The variable power source 286 and the rectifier 284 condition the AC power signal such that it is suitable to provide to the accelerometer 278. The acceleration circuit 282 further includes an oscillator 290 and an amplifier 292 in order to detect the acceleration of the accelerometer 278. The acceleration circuit 282 produces the acceleration signal 288 that is provided back to the variable power source 286 in the aforementioned feedback loop.

The acceleration circuit 282 may measure the displacement of the accelerometer 278 in a variety of ways. The acceleration circuit 282 may measure the changes in capacitances as the electrodes of the accelerometer 278 (not depicted) change in orientation to one another. Alternatively, the acceleration circuit 282 may measure capacitance imbalance generated on opposite sides of the accelerometer 278 as the proof mass is displaced. In a still further embodiment, a detector 294 may be used to detect the relatively low frequency acceleration signal of the motion of the proof mass as an envelope on the high frequency supply voltage signal.

Thus, in the embodiment depicted in 4C, the electronics 250 are split between the front end electronics 252 and the back end electronics 256. The front end electronics 252 are mechanically connected to the electrode 254, for example, by being mechanically connected to the substrate 276. The electrode signal 260 is provided from the electrode 254 and the front end electronics 252 to the back end electronics 256 by a lead wire 296. Therefore, the front end electronics 252 and the back end electronics 256 may range from a few centimeters to over a meter apart in distance. This distance would be covered by the lead wire 296. Alternatively, it is understood that the lead wire 296 may be replaced by any form of electrical signal connection, such as other forms of wired and/or wireless connections.

The alternative implementations of the electronics seek to take advantage of improved signal processing at a location close to the point of acquisition of the biopotential signal. By integrating the accelerometer with the electrode, the acceleration detected by the accelerometer closely resembles the motion forces experienced by the electrode during biopotential acquisition. This includes both motion artifacts due to the movement of the patient as well as artifacts due to the motion of the electrode itself. The improved processing of the biopotential signal prior to its transmission through an electrical lead reduces the susceptibility of the signal to motion or other electromagnetic artifacts from transmission across the lead wire. However, the implementation of the full processing circuitry on each electrode as depicted in FIG. 4B may increase the size, complexity, and costs of the finished electrode. Therefore, selection between the embodiments may depend upon a particular intended use or application of the electrode.

FIGS. 5A-D depict an alternative embodiment of an electrode as disclosed herein at various stages in the product process.

The electrode 300 begins as substantially a silicon substrate 302 to which a nitride layer 304 and a boron doped layer 306 are deposed. Next, a potassium hydroxide (KOH) etch is used to create the electrode cavity 308 out of the silicon substrate 302. The electrode cavity 308 is the start of what will be the microelectrode 314. Additionally, the potassium hydroxide etch is further used to etch out the proof-mass 310 for what will become the accelerometer 312. The boron doped layer 306 holds the proof-mass 310 in place after the silicon substrate 302 around it has been etched away. Additionally, a dry etch process is used to remove portions 318 of the boron doped layer 306 to create electrical isolation between what will become the microelectrode 314 and what will become the accelerometer 312.

Figure 5A:
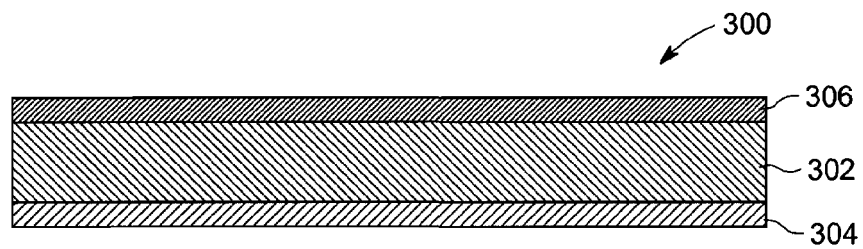
FIGS. 5A-5D depict a microelectrode at various stages of construction of the microelectrode.
Figure 5B:
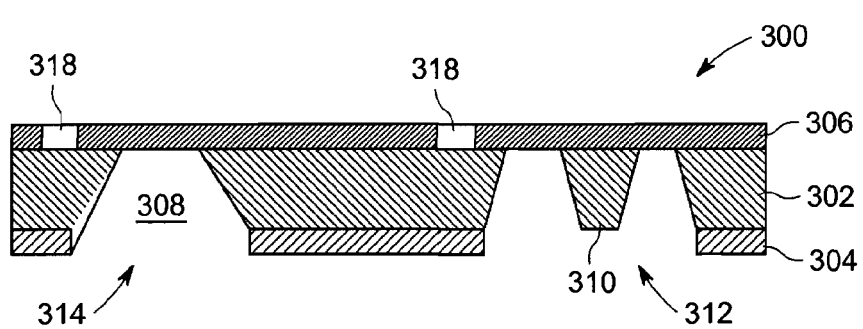
Figure 5C:
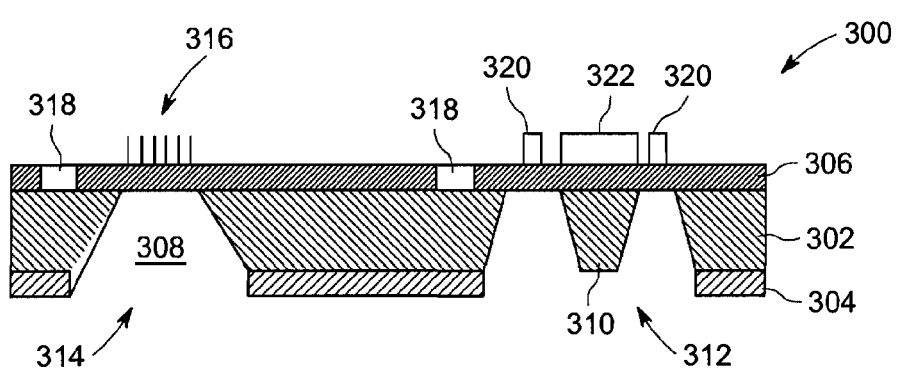
Figure 5D:
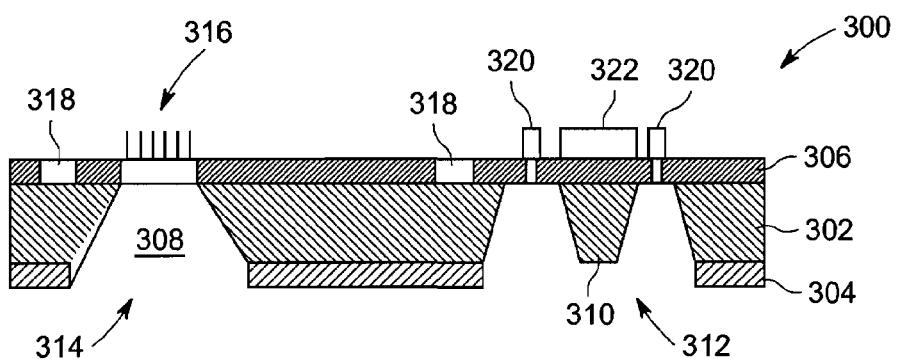

FIG. 5C depicts spikes 316 of the microelectrode 314 that are electroplated to the boron doped layer 306. The spikes 316 are electroplated with silver or silver/silver chloride for its signal transduction and hypoallergenic properties.

The spring 320 that will support the proof mass 310 is deposited on the boron doped layer 306. In this embodiment, the deposited spring 320 may be constructed of polysilicon. Alternatively, the spring 320 may be constructed of the bulk silicon substrate 302 and created during the potassium hydroxide etching process that was used to create the proof mass 310.

One or more electrodes 322 are electroplated on the boron doped layer 306. The electrodes 322 are those electrodes that sense the displacement of the proof mass 310 during acceleration.

Finally, sulphur hexafluoride ($SF_6$) dry etching is used to selectively remove the portions of the boron doped layer 306 upon which the spiked electrode 316, springs 320, and electrode 322 have been deposited or electroplated. The removing of the boron doped layer 306 releases the proof mass 310 such that it is supported by the springs 320 and is thus movable by the forces of acceleration. In the alternative embodiment wherein the springs 320 are constructed of etched bulk silicon, the release from the boron doped layer 306 produces a similar effect, suspending the proof mass 310 from the springs 320.

It is to be noted that the electrode 300 depicted in FIG. 5 further depicts an alternative embodiment of a horizontally arranged electrode, similar to that of FIG. 1, however, the electrode 300 is constructed from an integral silicon substrate whereas the electrode 10 of FIG. 1 is an assembly of individually constructed components. Additionally, while the above description of the construction of electrode 300 is intended to be merely exemplary of the processes by which the electrodes as disclosed herein can be constructed. One of ordinary skill in the art would recognize alternatives to the disclosed process, which is not intended to be limiting.

Figure 6:
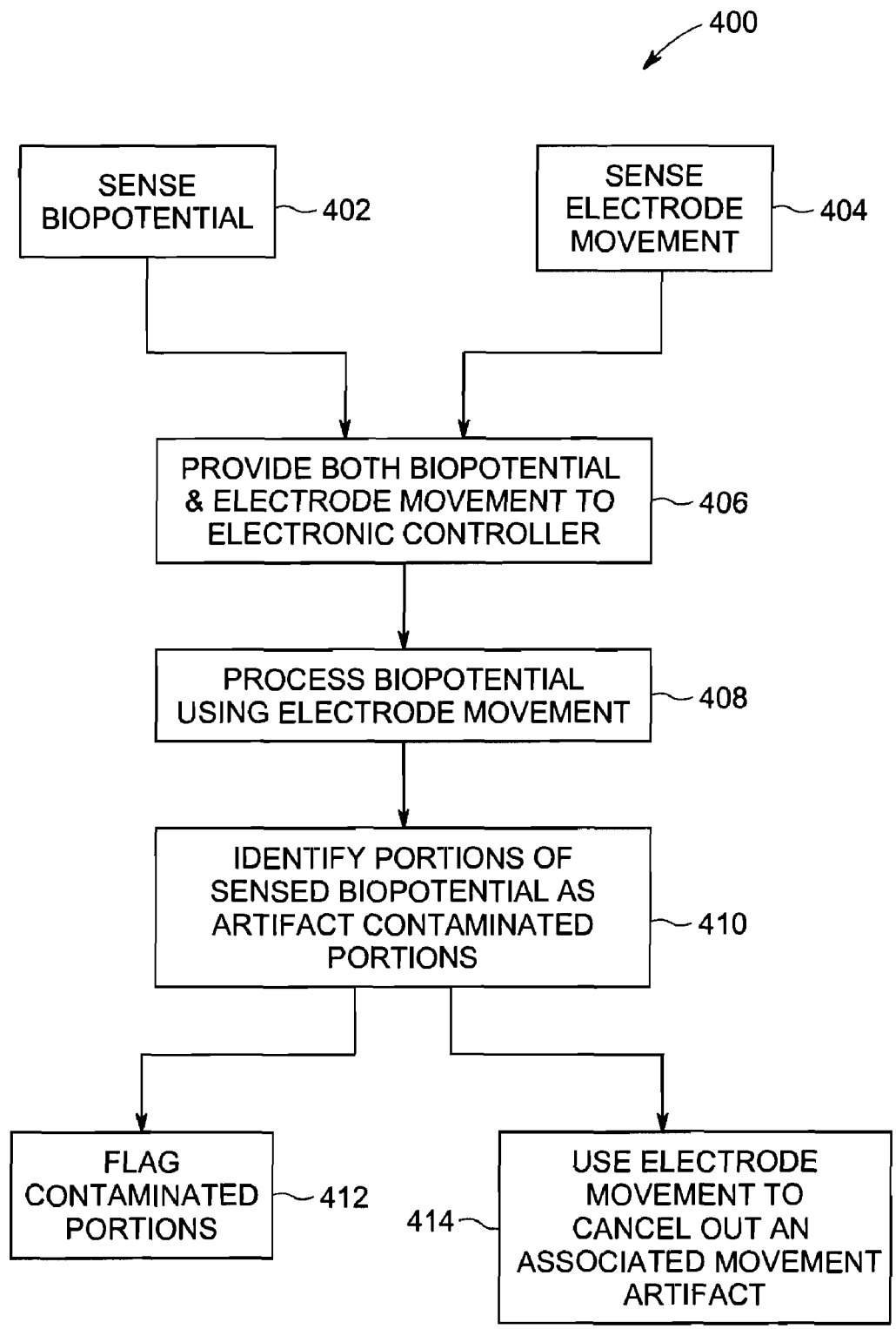
FIG. 6 is a flow chart depicting the steps of an embodiment of a method of measuring a biopotential.

FIG. 6 is a flow chart 400 depicting the steps of the embodiment of a method of measuring a biopotential. At 402 and 404, a biopotential is sensed and electrode movement is sensed 404. Both the biopotential and the movement are sensed on the same electrode and are sensed simultaneously, thus producing a movement signal that closely represents the actual movement of the electrode as the biopotential is sensed.

Next, at 406, both the biopotential and electrode movement signals are provided to an electronic controller. The electronic controller may be located within a range of a few centimeters to a few meters from the patient.

Next, at 408, the biopotential is processed using the electrode movement signal. The processing of the biopotential at 408 may include using the electrode movement signal to identify portions of the biopotential that are contaminated by motion artifacts at 410. If a portion of the biopotential is identified as being artifact contaminated, then at 412 the contaminated portions may be flagged such that both portions of the biopotential are disregarded or given lower weight in later analysis. Rather than flagging individual portions of the biopotential, the electronic controller may use the electrode movement signal to produce a biopotential signal quality indicy. The biopotential signal quality indicy may be an ongoing representation of the quality of the biopotential that is acquired. As would be understood, the presence of detected motion artifacts would reduce signal quality as represented by the indicy. The electrode movement signal may be used to cancel out the associated movement artifacts in the contaminated portions at 414. By acquiring an electrode movement signal at 404 that closely approximates the actual movement of the electrode during biopotential acquisition, the electrode movement signal can be effectively used to filter out the movement artifacts in the acquired biopotential.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. An electrode system for the measurement of biopotential signals, the system comprising:
   a substrate;
   a microelectrode electrically connected to the substrate, the microelectrode comprising a plurality of conductive spikes;
   an accelerometer integrally formed into the substrate;
   a conductive lead connected to the substrate, the conductive lead carrying a combined signal including a biopotential from the microelectrode and an acceleration signal from the accelerometer;
   a biopotential amplifier electrically connected to the conductive lead; and
   an acceleration measurement circuit electrically connected to the conductive lead.

2. The system of claim 1, further comprising an electronics electrically connected to the lead, the electronics possess processes the biopotential signal obtained by the microelectrode and the acceleration signal obtained by the accelerometer to improve the quality of the biopotential signals.

3. The system of claim 2 wherein the electronics use the acceleration signal to identify a motion artifact contaminated portion of the biopotential signal.

4. The system of claim 1, wherein the plurality of conductive spikes comprise silver or a silver/silver chloride coating.

5. The system of claim 1, wherein the accelerometer is a first accelerometer and further comprising a second accelerometer, both the first and second accelerometers being mechanically integrated with the substrate, the first accelerometer and the second accelerometer being oriented in the substrate to measure acceleration in at least two orthogonal directions.

6. The system of claim 1, wherein the electrode system measures electroencephalographic (EEG) biopotentials.

7. The system of claim 1, wherein the biopotential amplifier and the acceleration measurement circuit are integrated with the substrate.

8. The system of claim 7, wherein the acceleration measurement circuit comprises an acceleration detector front end and a back-end circuitry.

9. The system of claim 8, wherein the acceleration detector front end is integrated with the substrate and a power supply is the back-end circuitry and mechanically separated from the acceleration detector front end.

10. The system of claim 9, wherein the acceleration detector front-end and back-end circuitry communicate across at least one lead wire the at least one lead wire also used for the biopotential measurement.

11. An electrode system for the measurement of biopotential signals, the system comprising:
    a conductive substrate;
    a microelectrode physically and electrically connected to the conductive substrate, the microelectrode comprising a plurality of conductive spikes;
    an accelerometer integrally formed into the conductive substrate;
    an acceleration measurement circuit electrically connected by a first lead to the accelerometer, the acceleration measurement circuit provides a high frequency supply voltage to the accelerometer;
    a second lead connected between the conductive substrate and the acceleration measurement circuit, the second lead carrying a combined signal including a biopotential from the microelectrode and an acceleration signal from the accelerometer; and
    a biopotential amplifier electrically connected to the second lead.

12. The electrode system of claim 11, wherein the biopotential amplifier exhibits a high impedance to high frequency signals and the acceleration measurement circuit exhibits a high impedance to low frequency signals.

13. The electrode system of claim 12, wherein the acceleration signal from the accelerometer is the high frequency supply voltage, electrically modified by the accelerometer when motion is detected by the accelerometer.

* * * * *